(12) United States Patent
Sutterlin et al.

(10) Patent No.: US 10,954,182 B2
(45) Date of Patent: Mar. 23, 2021

(54) REACTIVE DISTILLATION PROCESS/EQUIPMENT FOR FATTY ACID ESTER HYDROLYSIS TO PRODUCE CARBOXYLIC ACID AND ALCOHOL

(71) Applicant: Inventure Renewables, Inc., Tuscaloosa, AL (US)

(72) Inventors: William Rusty Sutterlin, Tuscaloosa, AL (US); Ryan Alexander Long, Tuscaloosa, AL (US); Cory O'Neil Blanchard, Tuscaloosa, AL (US); Hayden Sawyer, Tuscaloosa, AL (US)

(73) Assignee: Inventure Renewables, Inc., Tuscaloosa, AL (US)

( * ) Notice: Subject to any disclaimer, the term of this patent is extended or adjusted under 35 U.S.C. 154(b) by 0 days.

(21) Appl. No.: 16/649,123

(22) PCT Filed: Sep. 20, 2018

(86) PCT No.: PCT/US2018/052020
§ 371 (c)(1),
(2) Date: Mar. 19, 2020

(87) PCT Pub. No.: WO2019/060591
PCT Pub. Date: Mar. 28, 2019

(65) Prior Publication Data
US 2020/0290944 A1  Sep. 17, 2020

Related U.S. Application Data

(60) Provisional application No. 62/561,020, filed on Sep. 20, 2017.

(51) Int. Cl.
C07C 51/09 (2006.01)
C07C 29/09 (2006.01)
(Continued)

(52) U.S. Cl.
CPC ............. *C07C 51/09* (2013.01); *B01J 19/24* (2013.01); *C07C 29/095* (2013.01); *C07C 51/44* (2013.01); *C07C 51/38* (2013.01); *C07C 51/445* (2013.01)

(58) Field of Classification Search
CPC ..... C07C 51/445; C07C 29/095; C07C 67/08; C07C 51/09; C07C 51/44; B01J 19/24
See application file for complete search history.

(56) References Cited

U.S. PATENT DOCUMENTS 5,770,770 A * 6/1998 Kim ..................... C07C 51/44
562/608
6,518,465 B2 * 2/2003 Hoyme .................. C07C 51/09
568/698
(Continued)

OTHER PUBLICATIONS

Young, International Search Report and Written Opinion for PCT/US2018/052020, dated Jan. 17, 2019.

*Primary Examiner* — Yate K Cutliff
(74) *Attorney, Agent, or Firm* — Greer, Burns & Crain, Ltd.

(57) ABSTRACT

Provided are processes and products of manufacture that provide a green solution to the hydrolysis of C8/C10 methyl ester to fatty acids. Provided are reactive distillation processes for producing an aliphatic acid and an alcohol as hydrolysis products. Provided are processes and products of manufacture encompassing the hydrolysis of fatty acid alkyl esters to an aliphatic acid and an alcohol by a reactive distillation process. Provided are processes and products of manufacture useful for equilibrium-limited reactions and for the separation of azeotropic mixtures. Provided are reactive distillation products of manufacture and processes for alkyl alkanoate hydrolysis comprising a reaction column comprising a rectifying rectifying zone for further distillation, a reaction zone, and a stripping zone wherein products are (Continued)

separated from reaction mixtures, where a water stream and fatty acid alkyl ester stream can be fed into the reaction section.

21 Claims, 2 Drawing Sheets

(51) Int. Cl.
*B01J 19/24* (2006.01)
*C07C 51/44* (2006.01)
*C07C 51/38* (2006.01)

(56) References Cited

U.S. PATENT DOCUMENTS

| | | | |
|---|---|---|---|
| 7,041,199 B1* | 5/2006 | Moritz | B01D 3/009 |
| | | | 203/29 |
| 7,652,167 B2* | 1/2010 | Miller | C07C 67/08 |
| | | | 560/179 |
| 9,045,412 B2* | 6/2015 | Sander | C07C 51/487 |
| 9,090,556 B2* | 7/2015 | Miller | C07C 67/08 |
| 2002/0077501 A1 | 6/2002 | Hoyme et al. | |
| 2002/0183549 A1 | 12/2002 | Lee | |
| 2006/0128991 A1 | 6/2006 | Michl et al. | |
| 2008/0128262 A1 | 6/2008 | Huang et al. | |
| 2014/0256985 A1 | 9/2014 | Sander et al. | |
| 2018/0118659 A1* | 5/2018 | Hiles | C07C 67/08 |

* cited by examiner

US 10,954,182 B2

REACTIVE DISTILLATION PROCESS/EQUIPMENT FOR FATTY ACID ESTER HYDROLYSIS TO PRODUCE CARBOXYLIC ACID AND ALCOHOL

RELATED APPLICATIONS

This application is a national phase application claiming benefit of priority under 35 U.S.C. § 371 to Patent Convention Treaty (PCT) International Application serial number PCT/US2018/052020, filed Sep. 20, 2018, now pending, which claims the benefit of priority to U.S. Provisional Application Ser. No. (USSN) 62/561,020, Sep. 20, 2017. The aforementioned applications are expressly incorporated herein by reference in their entirety and for all purposes.

TECHNICAL FIELD

This invention generally relates to the commercial distillation of organic compounds. In alternative embodiments, processes and products of manufacture as provided herein provide a green solution to the hydrolysis of C8/C10 methyl ester to fatty acids. In alternative embodiments, provided are reactive distillation processes for producing an aliphatic acid and an alcohol as hydrolysis products. In alternative embodiments, provided are processes and products of manufacture encompassing the hydrolysis of fatty acid alkyl (e.g., methyl) esters to an aliphatic acid (a carboxylic acid) and an alcohol (e.g., methanol) by a reactive distillation process. In alternative embodiments, processes and products of manufacture as provided herein are useful for equilibrium-limited reactions, such as hydrolysis and esterification, and for the separation of azeotropic mixtures. In alternative embodiments, provided are reactive distillation products of manufacture and processes for alkyl alkanoate (such as fatty acid alkyl ester, e.g., methyl ester) hydrolysis comprising (or comprising use of) a reaction column comprising a rectifying rectifying zone for further distillation, a reaction zone, and a stripping zone wherein products are separated from reaction mixtures, where in alternative embodiments a water stream and fatty acid alkyl ester stream is fed into the reaction section, and whereby the alcohol (e.g., methyl alcohol) and water is removed from the rectifying section. In alternative embodiments, the aliphatic acid (e.g., carboxylic acid) is removed from the reaction section.

BACKGROUND OF THE INVENTION

Currently octanoic and decanoic fatty acids are very desirable in the oleo chemical and personal care markets but are typically found in great quantity in their methyl ester form as methyl octanoate and methyl decanoate. They are typically sourced from coconut and palm kernel refined oils, where the oil is transesterified through the use of an alkaline catalyst, e.g. sodium methoxide and an alcohol, e.g., methanol, to make a mixed fatty acid methyl ester stream, comprised of C6-C18 chain lengths. The mixed stream is then taken through a series of fractional distillation units where the C6/C8/C10, C12/14, and C16/18 chain lengths methyl esters are purified and isolated. The C12/14 fatty acid methyl esters are then processed into fatty alcohols that are useful for detergents and personal care applications.

To convert the methyl octanoate and methyl decanoate back to their octanoic and decanoic fatty acid forms, the C8/C10 Methyl Ester stream is saponified through the use of a strong base, typically sodium hydroxide, and subsequently acidulated through the use of a strong acid reagent, sulfuric acid. The saponification/acidulation step of the C8/C10 methyl ester product produces a pure fatty acid stream at the expense of being relatively costly in terms of the reagents needed to complete the reaction (along with any equipment corrosion concerns associated with those acidic/alkaline reagents) and expensive waste disposal costs.

Since methyl octanoate and methyl decanoate are in the ester form, methyl octanoate and methyl decanoate are sold at a low price or saponified and acidulated to methanol and octanoic and decanoic fatty acids, which are more valuable but the cost and complexity of this method is high. It is therefore desirable to industry to have an low cost, simple and efficient process to convert the methyl octanoate and methyl decanoate from their ester form to their acid form and to purify them to a state substantially free of methanol without the use of saponification and acidulation.

Although reactive distillation has been known as one of unit operations since the 1920s, most of the reaction and distillation processes have been operated independently.

SUMMARY OF THE INVENTION

In alternative embodiments, provided are reactive distillation methods and industrial processes that optimize operating conditions for the hydrolysis of alkyl alkanoates.

In alternative embodiments, provided are reactive distillation methods and processes for producing an aliphatic acid and an alcohol as hydrolysis products from a composition,
  wherein the composition comprises: one or more (types of) alkyl alkanoate(s),
  and optionally the composition comprises more than about (or at least about) 10%, 20%, 30%, 40% or 50% by weight of the one or more alkyl alkanoate(s),
  wherein optionally the one or more alkyl alkanoate(s) comprises an alkyl octanoate, and optionally the alkyl octanoate comprises a methyl octanoate, or optionally the alkyl of the alkyl octanoate is between about C1 to C10 in length,
  wherein optionally the one or more alkyl alkanoate(s) comprises an alkyl decanoate, and optionally the alkyl decanoate comprises a methyl decanoate, or optionally the alkyl of the alkyl decanoate is between about C1 to C10 in length,
  wherein optionally the aliphatic acid produced by the reactive distillation process comprises an octanoic acid and/or a decanoic acid,
  and optionally the alcohol comprises a methanol, or an alcohol C1 to C10 in length,
  comprising the steps of:
  (a) (i) hydrolyzing said composition to an aliphatic acid (wherein optionally the aliphatic acid comprises an octanoic acid and/or a decanoic acid) and an alcohol (wherein optionally the alcohol comprises a methanol or an alcohol C1 to C10 in length) in a reaction zone under conditions comprising:
  (1) a temperature of between about 100° C. to 300° C., 50° C. to 400° C., or 150° C. to 450° C.;
  (2) a pressure of between about 100 psi to 1,500 psi, or 1,000 psi to 5,000 psi; and/or
  (3) a time of between about 0.1 hours (hr) to 100 hr, 5 seconds to 10 minutes, or 1 minute to one hour, or
  (ii) (1) providing or having provided a composition comprising one or more (types of) alkyl alkanoate(s), and
  (2) hydrolyzing or having hydrolyzed said composition to an aliphatic acid in a reaction zone under conditions comprising:

(1) a temperature of between about 100° C. to 300° C., 50° C. to 400° C., or 150° C. to 450° C.;

(2) a pressure of between about 100 psi to 1,500 psi, or 1,000 psi to 5,000 psi; and/or (3) a time of between about 0.1 hours (hr) to 100 hr, 5 seconds to 10 minutes, or 1 minute to one hour;

(b) continuously injecting or introducing the one or more (types of) alkyl alkanoate(s) with or without water into the reaction zone under pressure or by vacuum or by injecting; or, introducing the one or more (types of) alkyl alkanoate(s) into the reaction together with water, or the water and the one or more (types of) alkyl alkanoate(s) are injected or introduced separately into the reaction zone, under pressure or by vacuum, wherein optionally, of pressure is used to inject or introduce the one or more (types of) alkyl alkanoate(s), the pressure comprises the pressure of the reaction zone (e.g., at the bottom of a column), and optionally the pressure comprises the pressure of the reaction zone plus friction losses, and optionally the temperature is an ambient temperature or at between about 100° C. to 300° C., 50° C. to 400° C., or 150° C. to 450° C.; and (c) at the same time (or continuous with) said step (b), collecting said reaction mixture from said lower portion of said reaction zone, wherein optionally the reaction mixture is removed from said lower portion of said reaction zone because of the internal pressure of the reaction vessel or by using a pump, and optionally separating said reaction mixture into aliphatic acid and alcohol, with water in one or multiple phases, wherein optionally the reaction zone is configured as a (or is within) a column, and the column comprises stages (wherein the stages optionally comprise trays or a structured packing) inside the column, and optionally the column comprises side streams at multiple points along the column at different stages for removal of different materials, where each side stream comprises removal of a different composition, and optionally the separating comprises reboiling in a reboiler, wherein optionally the reboiler operates in a range of temperature from between about 100° C. to 300° C., and optionally the reboiler operates in a range of pressure of between about 100 psi to 1,500 psi, or optionally the reboiler operates in a range of temperature from between about 100° C. to 300° C. and in a range of pressure of between about 100 psi to 1,500 psi.

In alternative embodiments of methods as provided herein, the reaction zone can be comprised of one or multiple plug flow reactors preceding the reactive distillation unit, and optionally alcohol and/or water removal can occur during and/or after any plug flow reaction step, and optionally water addition can occur during and/or after any plug flow reaction step.

In alternative embodiments, methods as provided herein comprise use of a product of manufacture or a reactive distillation unit for alkyl alkanoate hydrolysis, wherein: (a) the product of manufacture or the reactive distillation unit comprises a condenser wherein vapor flows are condensed to liquids, a reactive distillation column, and a reboiler; and/or, (b) the reactive distillation unit comprises: at least one reactive distillation column comprising three zones: a rectifying zone for further distillation, a reaction zone, and a stripping zone wherein products are separated from reaction mixtures.

In alternative embodiments of methods as provided herein, a catalyst is used in any reaction zone, including plug flow reactors, in the rectifying zone and/or in the stripping zone, optionally to enhance the hydrolysis kinetics and/or equilibrium of alkyl alkanoate(s).

In alternative embodiments, provided are products of manufacture or a reactive distillation unit for alkyl alkanoate hydrolysis comprising: a condenser, wherein vapor flows are condensed to liquids, at least one reactive distillation column, and a reboiler, wherein the reactive distillation unit comprises at least one reactive distillation column comprising three zones: a rectifying zone for further distillation, a reaction zone, and a stripping zone wherein products are separated from reaction mixtures.

In alternative embodiments of the products of manufacture or reactive distillation units as provided herein, wherein the product of manufacture or reactive distillation unit is manufactured or configured to practice a process of any of the preceding claims, or as manufactured or configured as set forth in FIG. 1.

Other features and advantages of the present invention will become more apparent from the following detailed description, taken in conjunction with the accompanying drawings which illustrate the principles of the invention. It should be understood, however, that the detailed description and specific examples, while indicating preferred embodiments of this invention, are given by way of illustration only, since various changes and modifications within the spirit and scope of the invention will become apparent to those skilled in the art from this detailed description.

All publications, patents, patent applications cited herein are hereby expressly incorporated by reference for all purposes.

BRIEF DESCRIPTION OF THE DRAWINGS

The drawings set forth herein are illustrative of exemplary embodiments provided herein and are not meant to limit the scope of the invention as encompassed by the claims.

Like reference symbols in the various drawings indicate like elements.

DETAILED DESCRIPTION

Figure 1:
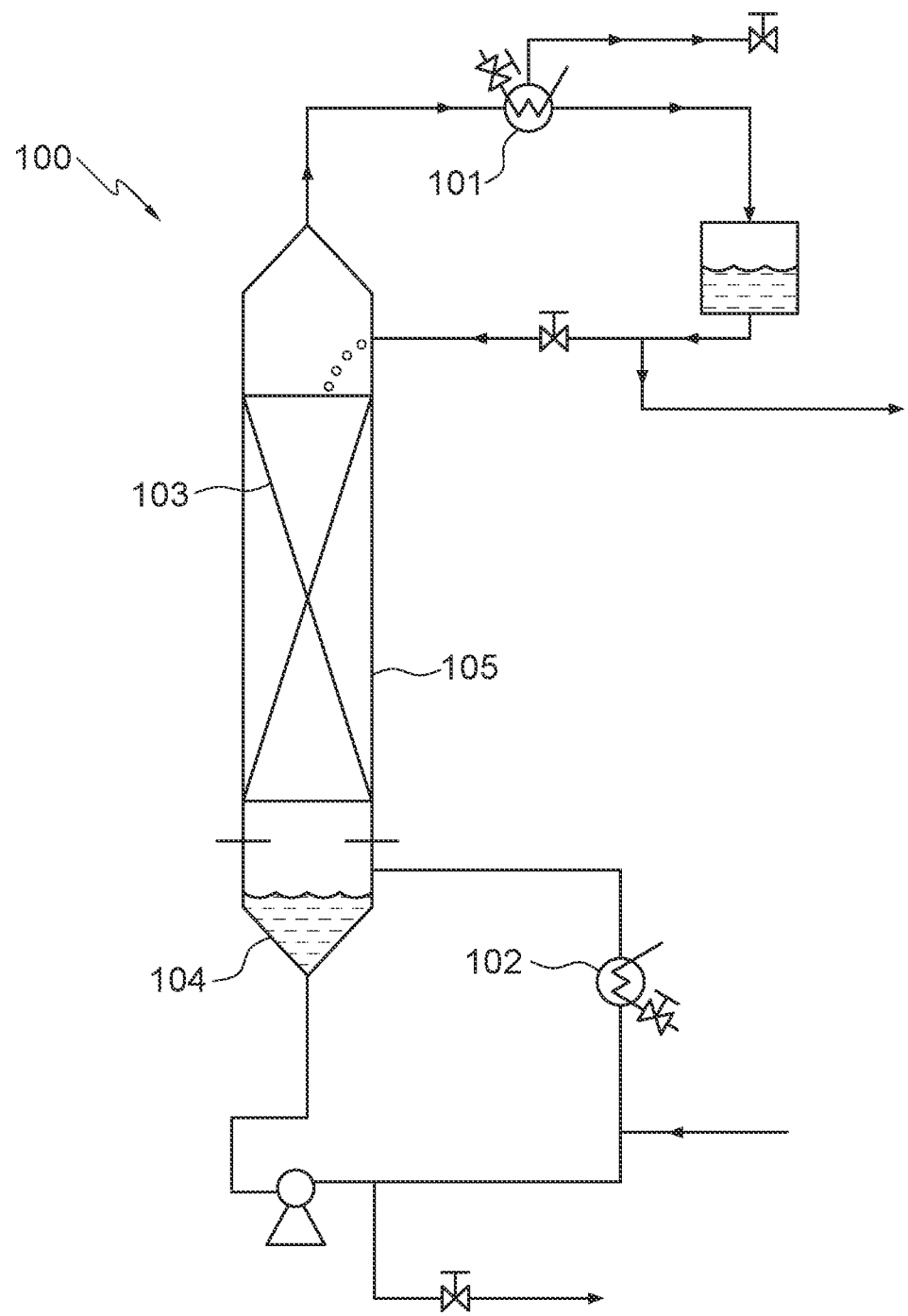
FIG. 1 illustrates a schematic representation of an exemplary reactive distillation configuration for carrying out a reactive distillation process, wherein the configuration (or product of manufacture) comprises: a condenser 101, wherein vapor flows are condensed to liquids; at least one reactive distillation column 100, and a reboiler 102, wherein the reactive distillation column 100 comprises three zones: a rectifying zone 103 for further distillation (or separation), a reaction zone 104, and a stripping zone 105 wherein products are separated from reaction mixture.

In alternative embodiments, processes and products of manufacture as provided herein provide a green solution to the hydrolysis of C8/C10 methyl ester to fatty acids. In alternative embodiments, processes and products of manufacture as provided herein use a reactive distillation that can fully hydrolyze a C8/C10 ester in a pressurized distillation column, with or without the use of strong acidic resin or use of solid state heterogenous acid catalyst to help reduce temperatures/pressures required.

In alternative embodiments, in processes and products of manufacture as provided herein, alcohol (e.g., methanol) is created from the hydrolysis reaction (example: FAME+Water=FFA+Methanol), and optionally the alcohol (e.g., methanol) and water are immediately stripped off the bottom of the distillation column and rectified through its internal stages, producing a pure alcohol (e.g., methanol) stream as the distillate fraction of the unit while pushing the reaction to completion—all at the same time. In alternative embodiments, the water is removed as a separate point on the column or is removed as a mixture with the alcohol. In alternative embodiments, the temperature of the bottom can range from between about 100° C. to 300° C. with residence times ranging from between about 0.01 hours to 100 hours, along with pressure ranging from between about 0 pounds per square inch absolute (psia) to 2,000 psia. In alternative embodiments, the temperature of the bottom ranges from between about 200° C. to 300° C. with residence times ranging from between about 1 hours to 10 hours along with pressure ranging from between about 500 psia to 1,000 psia. Also, the use of a non-condensable stripping gas may or may not be present in the distillation unit.

In alternative embodiments, in practicing processes and products of manufacture as provided herein, a full conversion from C8/C10 methyl esters to free fatty acids can be achieved in one unit operation rather than multiple pieces of equipment, making it ideal as a bolt-on for many current active plant operations. In addition to eliminating costly acidic/alkaline reagents, practicing processes and products of manufacture as provided herein can provide drastically improved equipment lifetime, has no waste water concerns, as well as produces a usable, purified alcohol (e.g., methanol) stream that can be recycled upstream of the process for further transesterification of refined coconut and palm kernel oil.

In alternative embodiments, a special characteristic of processes and products of manufacture as provided herein is the premixture of the single feed stream of alkyl octanoate and alkyl decanoate and water to the reactive distillation column under pressure. Reactive distillation under pressure provides for keeping the fatty acids at the bottom of the column whereby at the same time the alcohol present, even under significant pressure will enter the rectification column and be removed. In alternative embodiments, the hydrolysis reaction occurs in reflux state at the bottom of the column and in the packing. In alternative embodiments, the molar ratio of water to fatty acid methyl ester is varied from 0.01 parts to 1000 parts, or 0.1 parts to 500 parts, or 1 part to 100 parts, by weight water to fatty acid methyl ester; fatty acid ethyl ester, fatty acid propyl ester or fatty acid butyl ester or any mixtures thereof.

In alternative embodiments, suitable strongly acidic ion exchange resins are styrene and acrylic resins having sulfonic acid groups ($-SO_3H$) attached to an insoluble styrenic or acrylic polymer matrix. In alternative embodiments, conventional resins are used where bead size is so small that the resin and inert polymers are molded together into a conventional packing shape, and resins and molding processes that can be used include e.g., a Raschig ring, Berl saddle, Intalox saddle or Pall ring, using conventional molding processes. The packing can be then located or embedded in the reaction zone.

In alternative embodiments, between about 0.01% to 50% by weight of the inert polymers are added to the ion exchange resin. In alternative embodiments, the number of theoretical plates is between about 1 to 500. In alternative embodiments, between about 5 to 100 plates are used for the rectifying zone, or between about 0 to 100 plates are used for the reaction zone. In alternative embodiments, provided herein are reactive distillation processes without a rectifying zone whereby the alcohol (e.g., methanol) water is removed as a mixture.

In alternative embodiments, reflux ratio is an important factor in distillation tower design and operation. To increase reaction yield and selectivity, in alternative embodiments, the condensed liquids are totally or substantially recycled to the column.

In alternative embodiments, an important operating factor is the temperature of the reboiler. In alternative embodiments, the reboiler can have a range of temperature from between about 100° C. to 300° C. In alternative embodiments, another important operating factor can be the pressure of the reboiler, which can operate at a range of pressure from between about 100 psi to to 1,500 psi.

Figure 2:
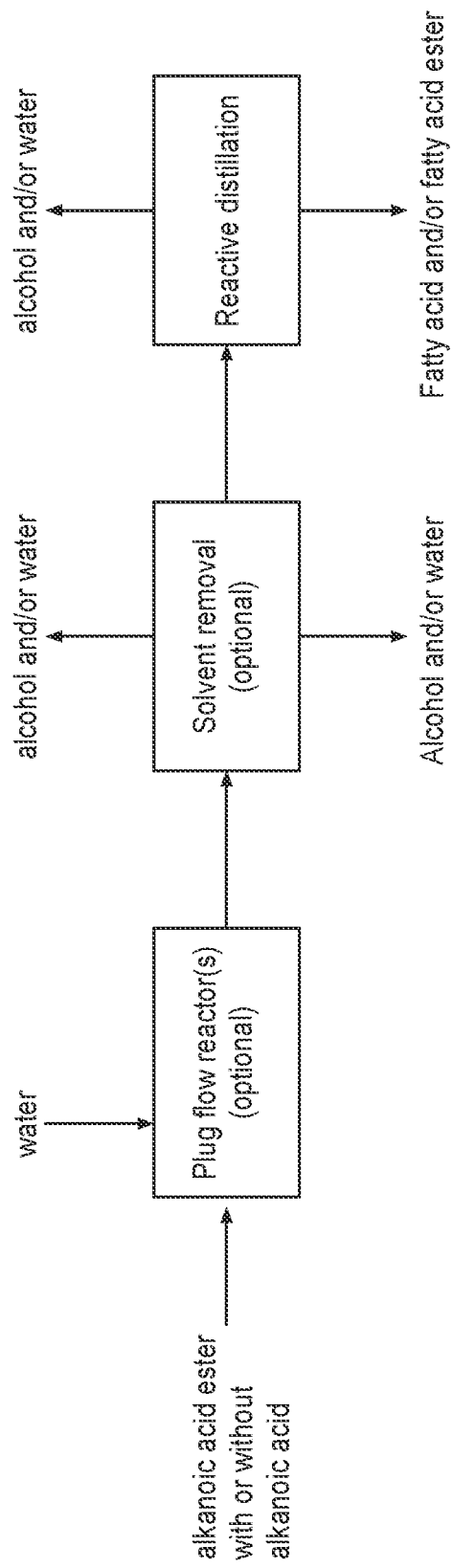
FIG. 2 illustrates a schematic flow chart of an exemplary process as provided herein.

In alternative embodiments, the reaction zone can be comprised of one or multiple plug flow reactors preceding the reactive distillation unit, e.g., as illustrated in the schematic flow diagram of FIG. 2.

A number of embodiments of the invention have been described. Nevertheless, it can be understood that various modifications may be made without departing from the spirit and scope of the invention. Accordingly, other embodiments are within the scope of the following claims.

What is claimed is:

1. A reactive distillation process for producing an aliphatic acid and an alcohol as hydrolysis products from a composition,
   wherein the composition comprises: one or more alkyl alkanoate(s),
   comprising the steps of:
   (a) (i) hydrolyzing said composition to an aliphatic acid in a reaction zone under conditions comprising:
       (1) a temperature of between about 100° C. to 300° C., 50° C. to 400° C., or 150° C. to 450° C.;
       (2) a pressure of between about 100 psi to 1,500 psi, or 1,000 psi to 5,000 psi; and/or
       (3) a time of between about 0.1 hours (hr) to 100 hr, 5 seconds to 10 minutes, or 1 minute to one hour, or
   (ii)
       (1) providing or having provided a composition comprising one or more (types of) alkyl alkanoate(s), and
       (2) hydrolyzing or having hydrolyzed said composition to an aliphatic acid in a reaction zone under conditions comprising:
           (1) a temperature of between about 100° C. to 300° C., 50° C. to 400° C., or 150° C. to 450° C.;
           (2) a pressure of between about 100 psi to 1,500 psi, or 1,000 psi to 5,000 psi; and/or
           (3) a time of between about 0.1 hours (hr) to 100 hr, 5 seconds to 10 minutes, or 1 minute to one hour;
   (b)
   (i) continuously injecting or introducing the one or more alkyl alkanoate(s) with or without water into the reaction zone under pressure or by vacuum or by injecting;
   (ii) introducing the one or more alkyl alkanoate(s) into the reaction together with water, or
   (iii) the water and the one or more alkyl alkanoate(s) are injected or introduced separately into the reaction zone, under pressure or by vacuum; and
   (c) at the same time or continuous with said step (b), collecting said reaction mixture from said lower portion of said reaction zone, and
   (d) the reaction zone is comprised of a multiple plug flow reactor preceding the reactive distillation unit.

2. The method of claim 1, wherein the reaction zone is comprised of multiple plug flow reactors preceding the reactive distillation unit.

3. The method of claim 1, comprising use of a product of manufacture or a reactive distillation unit for alkyl alkanoate hydrolysis, wherein:
 (a) the product of manufacture or the reactive distillation unit comprises a condenser wherein vapor flows are condensed to liquids, a reactive distillation column, and a reboiler; and/or
 (b) the reactive distillation unit comprises: at least one reactive distillation column comprising three zones: a rectifying zone for further distillation, a reaction zone, and a stripping zone wherein products are separated from reaction mixtures.

4. The method of claim 1, wherein a catalyst is used in a reaction zone.

5. The method of claim 1, wherein the composition comprises more than about or at least about 10% by weight of the one or more alkyl alkanoate(s).

6. The method of claim 5, wherein the composition comprises more than about or at least about 50% by weight of the one or more alkyl alkanoate(s).

7. The method of claim 1, wherein the one or more alkyl alkanoate(s) comprises an alkyl octanoate.

8. The method of claim 7, wherein the alkyl octanoate comprises a methyl octanoate.

9. The method of claim 7, wherein the alkyl octanoate is between about C1 to C10 in length.

10. The method of claim 1, wherein the aliphatic acid produced by the reactive distillation process comprises an octanoic acid and/or a decanoic acid.

11. The method of claim 1, wherein the alcohol comprises a methanol, or an alcohol C1 to C10 in length.

12. The method of claim 1, wherein the method comprises hydrolyzing the composition to an aliphatic acid comprising an octanoic acid and/or a decanoic acid.

13. The method of claim 1, wherein the method comprises hydrolyzing the composition to an alcohol comprising a methanol or an alcohol C1 to C10 in length.

14. The method of claim 1, wherein in step (b):
 (a) the pressure used to inject or introduce the one or more alkyl alkanoate(s) comprises the pressure of the reaction zone at the bottom of a column,
 (b) the pressure used to inject or introduce the one or more alkyl alkanoate(s) comprises the pressure of the reaction zone plus friction losses, and/or
 (c) the temperature is an ambient temperature or at between about 100° C. to 300° C., 50° C. to 400° C., or 150° C. to 450° C.

15. The method of claim 1, wherein in step (c):
 (a) the reaction mixture is removed from said lower portion of said reaction zone because of the internal pressure of the reaction vessel or by using a pump;
 (b) the method comprises separating said reaction mixture into an aliphatic acid and alcohol, with water in one or multiple phases;
 (c) the separating comprises reboiling in a reboiler; or
 (d) and combination of (a) to (c).

16. The method of claim 2, wherein alcohol and/or water removal occurs during and/or after any plug flow reaction step.

17. The method of claim 2, wherein water addition occurs during and/or after any plug flow reaction step.

18. The method of claim 4, wherein the reaction zone comprises a plug flow reactor, a rectifying zone or a stripping zone.

19. The method of claim 4, wherein the catalyst is used in a reaction zone to enhance the hydrolysis kinetics and/or equilibrium of alkyl alkanoate(s).

20. The method of claim 15, wherein in step (b):
 (a) the reaction zone is configured as a or is within a column, and the column comprises stages inside the column,
 (b) the column comprises side streams at multiple points along the column at different stages for removal of different materials, where each side stream comprises removal of a different composition, or
 (c) the stages comprise trays or a structured packing.

21. The method of claim 15, wherein in step (c):
 (a) the reboiler operates in a range of temperature from between about 100° C. to 300° C.,
 (b) the reboiler operates in a range of pressure of between about 100 psi to 1,500 psi, or
 (c) the reboiler operates in a range of temperature from between about 100° C. to 300° C. and in a range of pressure of between about 100 psi to 1,500 psi.

\* \* \* \* \*